US009006684B2

(12) United States Patent
Laitinen et al.

(10) Patent No.: US 9,006,684 B2
(45) Date of Patent: Apr. 14, 2015

(54) SAMPLE MEASUREMENT SYSTEM

(75) Inventors: Jyrki Laitinen, Kuusisto (FI); Petri Kivelä, Piispanristi (FI)

(73) Assignee: PerkinElmer Singapore Pte. Ltd., Singapore (SG)

( * ) Notice: Subject to any disclaimer, the term of this patent is extended or adjusted under 35 U.S.C. 154(b) by 1328 days.

(21) Appl. No.: 12/738,843

(22) PCT Filed: Oct. 8, 2008

(86) PCT No.: PCT/FI2008/050559
§ 371 (c)(1),
(2), (4) Date: Apr. 20, 2010

(87) PCT Pub. No.: WO2009/056669
PCT Pub. Date: May 7, 2009

(65) Prior Publication Data
US 2011/0049385 A1 Mar. 3, 2011

Related U.S. Application Data

(60) Provisional application No. 61/001,121, filed on Oct. 31, 2007.

(51) Int. Cl.
*G01J 1/58* (2006.01)
*G01N 21/64* (2006.01)
(Continued)

(52) U.S. Cl.
CPC .............. *G01N 21/6452* (2013.01); *G01J 3/02* (2013.01); *G01J 3/0218* (2013.01); *G01J 3/0297* (2013.01);*G01J 3/10* (2013.01); *G01J 3/18* (2013.01); *G01J 3/4406* (2013.01); *G01N 21/253* (2013.01);
(Continued)

(58) Field of Classification Search
CPC ............ G01N 21/253; G01N 21/6452; G01N 21/6428; G01J 3/10; G01J 3/18; G01J 3/0218

USPC ................................ 356/19; 250/458.1, 461.2
See application file for complete search history.

(56) References Cited

U.S. PATENT DOCUMENTS 3,806,259 A * 4/1974 Boostrom et al. ............ 356/244
5,475,221 A 12/1995 Wang
(Continued)

FOREIGN PATENT DOCUMENTS

DE 19709377 Y 9/1998
EP 1403675 A 3/2004
(Continued)

OTHER PUBLICATIONS

Schena, Microanalysis of DNA: A practical approach, Oxford University Press, 1999, pp. 19-21.*

*Primary Examiner* — Yara B Green
(74) *Attorney, Agent, or Firm* — Seppo Laine Oy; Joshua P. Wert

(57) ABSTRACT

The invention relates to an apparatus and method for optically analyzing samples contained in sample sites of a sample holder by means of fluorescence. The apparatus comprises a first light source comprising a plurality of individual light sources having narrow wavelength bands, means for further limiting wavelength bands of the light emitted by the individual light sources, means for guiding the reduced-wavelength light to the sample sites of the sample holder, and a detector for detecting light from the sample sites. According to the invention said means for further reducing the wavelength bands emitted by the individual light sources comprise a wavelength-tunable single monochromator. The invention allows manufacturing of a microplate reader having the capability for fluorescence measurements at a continuous wavelength range, while maintaining the cost of the device at a reasonable level.

14 Claims, 5 Drawing Sheets

(51) Int. Cl.
*G01J 3/02* (2006.01)
*G01J 3/10* (2006.01)
*G01J 3/18* (2006.01)
*G01J 3/44* (2006.01)
*G01N 21/25* (2006.01)

(52) U.S. Cl.
CPC .... *G01N 21/6428* (2013.01); *G01N 2021/6419* (2013.01); *G01N 2021/6421* (2013.01); *G01N 2021/6471* (2013.01); *G01N 2021/6484* (2013.01); *G01N 2201/0627* (2013.01); *G01N 2201/0806* (2013.01)

(56) References Cited

U.S. PATENT DOCUMENTS

| | | |
|---|---|---|
| 6,097,025 A | 8/2000 | Modlin et al. |
| 2002/0037149 A1 | 3/2002 | Chen |
| 2003/0038248 A1 | 2/2003 | Maher |
| 2003/0062485 A1 | 4/2003 | Fernandez |
| 2004/0081621 A1 | 4/2004 | Arndt et al. |
| 2005/0122521 A1* | 6/2005 | Katzlinger et al. ........... 356/436 |
| 2005/0168742 A1* | 8/2005 | Jung et al. ................... 356/419 |
| 2006/0121602 A1 | 6/2006 | Hoshizaki |
| 2006/0122521 A1 | 6/2006 | Chen |
| 2006/0238764 A1 | 10/2006 | Hafeman |
| 2007/0098594 A1 | 5/2007 | Elkin et al. |
| 2007/0285643 A1* | 12/2007 | Wedowski et al. ............. 355/67 |
| 2008/0191149 A1* | 8/2008 | Zimenkov et al. ......... 250/492.1 |

FOREIGN PATENT DOCUMENTS

| | | |
|---|---|---|
| WO | WO 99/23466 | 5/1999 |
| WO | WO 01/11343 | 2/2001 |
| WO | WO2009/056669 | 5/2009 |

* cited by examiner

SAMPLE MEASUREMENT SYSTEM

BACKGROUND OF THE INVENTION

1. Field of the Invention

The invention relates to optical sample detectors used in various fields of life and analytical sciences, in particular medical and biomedical assays. In particular, the invention relates to fluorescence-based sample analysers.

2. Prior Art

Fluorescence analysers or the present kind are commonly adapted to detect light successively from each one of a plurality of sample sites contained in the microplate. Therefore, they are frequently called as microplate "readers". One example or such a system is the EnVision-reader and its variants available from PerkinElmer.

The present commercial microplate readers typically include a broad-band excitation light source. Before guiding the light emitted by the light source to a sample, the bandwidth of the light is regulated by filters, monochromators, or both. In prior art devices, high-quality dichroic filters and double monochromators are used.

US 2003/0081207 and U.S. Pat. No. 6,232,608 disclose devices including a plurality of optical filters and a monochromator arranged in series for selecting the desired wavelength. A disadvantage of such devices is that they require a large number of filters in order to be operable on a wide wavelength range. Therefore, if a new fluorescent marker, for example, is taken into use, also the filter bank of the device must be updated accordingly in order to get the best possible measurement results. However, the right filter having a sufficiently high quality may not always be at hand.

Devices having double monochromators installed in both the excitation and emission sides are disclosed in WO 00/63680 and US 2002/0109841. Double monochromators increase the wavelength-selectivity to a reasonable level but at the same time greatly increase the costs of the device.

WO 2005/057187 discloses a device having several different wavelength LEDs mounted to a rotatable wheel used as a moveable support, a rotatable wavelength filter wheel or moveable slide, which includes a plurality of optical filters having predefined transmit wavelengths. Therefore, the device is provided with a conventional filter bank, from which a filter having predefined transmission properties is chosen. Thus the abovementioned problem relating to using and availability of filters remain.

BioTek Instruments Inc. has published a Synergy™ 4 Multi-Detection Microplate Reader. The system is provided with a Xenon flash as its light source and it contains two double monochromators.

US 2007/0098594 discloses a fluorescence measurement apparatus where the excitation light is produced using discrete wavelengths obtainable by lasers. Thus, there is no need for wavelength filtering. A drawback of this arrangement is that the set of wavelengths which can be used for excitation is very limited.

Light emitting diodes have also been used in apparatuses designed for other purposes than fluorescence measurements. U.S. Pat. No. 5,475,221 discloses an apparatus having an array of LEDs and an Acousto-Optic Tunable Filter (AOTF) controlled by multiplexing means to obtain a broadband spectrometer. DE 19709377 discloses a luminescence measurement system having an ultraviolet LED as a light source. Light may be filtered before guiding it to a sample. The system allows for improved measurement of luminescence decay times. Neither of these apparatuses is suitable for fluorescence measurements.

SUMMARY OF THE INVENTION

It is an aim of the invention to achieve an improved microplate reader having the capability for fluorescence measurements at a continuous wavelength range, while maintaining the cost of the device at a reasonable level. In particular, it is an aim of the invention to provide a plate reader which has an improved optical performance in contrast to known devices in the same price category.

The invention is based on the idea of providing, in the excitation side of the apparatus, a first light source comprising a plurality of individual relatively narrow-band light sources, such as light emitting diodes (LEDs), having different emission bands, and a wavelength-tunable monochromator for further limiting the wavelength of the light originating from one of the narrow-band light sources conveyed to the sample. Further, the apparatus comprises means for conveying the light passing through the tunable monochromator to a sample plate or the like.

According to one embodiment, the narrow-band light sources are narrow-band LEDs (light emitting diodes). The LEDs may be further arranged in a multiple-wavelength module, from which one light from one LED at a time can be lead to the monochromator. The selection of the source LED may be carried out using a optical source selector separate from the LED module or by incorporating the LEDs into a combined narrow-band light source/selector module.

The narrow-band light sources typically have an emission band less than 100 nm, in particular 30-70 nm (at 10% intensity level).

According to one embodiment, the monochromator is a single monochromator, in contrast to double or higher order tandem monochromators typically used in high-performance plate readers.

According to one embodiment, the light directed to the sample can be individually selected to originate from one of the narrow-band light sources at a time.

In addition the first light source, the device may include wide-band light sources for enabling absorption measurements further to fluorescence measurements. For selecting the desired mode of operation, there may be provided an optical relay suitable for optically coupling one of more optical input lines to an optical output line or to several output lines at a time.

The narrow-band light source used for excitation, i.e., in the exemplary embodiment the LED used, is chosen based on the properties of the marking agent (marker) used in the sample. That is, the emission wavelength band of the source is such that it covers the absorption wavelength of the marker but does not overlap with the emission wavelength of the marker. In practice, an optimization algorithm taking into account both these criteria may be used such that the best possible signal-to-noise ratio is achieved.

On emission side of the device, there are means for collecting the light emitted by the sample due to the excitation, and means for detecting the intensity of the collected light.

According to one embodiment, a light relay is provided also on the emission side in order to allow for selecting a light detector most suitable for the intensity and/or wavelength of the emitted light and/or the goals of the measurement. Thus, a plurality of detectors may be used.

The emission side typically has a second monochromator for efficiently picking from the emission signal the marker emission wavelength of interest.

The monochromators on the excitation and on the emission sides may be diffraction grating-based adjustable monochromators. For example, Czerny-Turner monochromators are suitable for the purposes of the invention. On the excitation side it is the tuning range of the monochromator should extend over the usable bandwidth range of the narrow-band light sources.

Because grating-based monochromators, as is commonly known, pass through also higher diffraction order wavelengths, a filter or filters may be provided to prevent these undesired wavelengths from propagating to the sample. According to one embodiment, the apparatus automatically selects a right band-pass filter, depending on the wavelength of the narrow-band excitation light source used, for preventing any expected higher order interfering radiation from the excitation and/or the emission monochromator to pass the sample and/or the detector. However, conventional band-pass filters are in this embodiment not used for any other purpose.

According to one embodiment, light is produced at such a narrow wavelength band that even higher order diffraction blocking is not needed at the excitation and/or the emission side of the apparatus.

The invention offers significant benefits, as we have found that a very clean excitation signal can be formed at a significantly reduced cost level. The cost benefit results mainly from the fact that there is no need for second-order blocking of undesired wavelengths, and a single monochromator suffices. The quality of the excitation signal reflects to the emission (detection) side of the device as a more marker-specific emission signal. Ultimately, the throughput of the apparatus can be improved as the measurement time of a single sample well can be kept short.

The invention allows one to use an excitation light source which does not emit light practically at all at the emission wavelength of the marking agent. This is a significant benefit because in conventional apparatuses the excitation light source produces most of the undesired stray light hitting the sample and ultimately the detector. Thus, the combination of narrow-band light sources, such as LEDs and a single monochromator has proven to be surprisingly good as far as the amount of stray light and the costs of the device are concerned.

The present invention offers the benefit that the excitation wavelength can be continuously selected, in addition to the abovementioned benefits of low cost and good performance. Thus, the disadvantage of having to limit the possible excitation light at discrete wavelengths only, as when dichroic filters are used, is overcome. On the other hand, relatively inexpensive single monochromators can be used. Single monochromators provide monochromatization of the optical signal of only about 4 orders of magnitude, which is insufficient when used with broadband light sources. This is why prior art devices include additional band-limiting filters or double/tandem monochromators having two or more monochromators arranged in series.

In a further embodiment of the invention, the apparatus comprises
  a first light source, which is the multiple-narrow band light source described above, and at least one second light source,
  a monochromator having an input to which first light source is optically connected or connectable and an output for monochromatized light,
  light guiding means for guiding light originating from the first and from the at least one second light sources to the sample sites,
  a detector for detecting light from the sample sites, and
  a light relay comprising
  a first input optically connected to the output of the monochromator,
    at least one second input optically connected or connectable to a second light source, and
    a first output for guiding light from selected input of the light relay to the sample sites.

According to one embodiment, the light relay further comprises a second output, the first and second outputs being adapted for guiding light from selected input of the light relay to the sample sites optionally from above or from below of the sample holder.

According to one embodiment, the light relay includes a plurality of light inputs arranged in circumferential manner to an input member and a plurality of light outputs arranged in circumferential manner on an output member. Further, the relay allows the inputs to be optically connected to the outputs one at a time, depending on the desired measurement mode, by the relative rotation of the input and output members.

According to one embodiment, the input member or the output member is a rotatable wheel comprising a plurality of connection slots for optic fibers.

According to one embodiment, the input and output members are arranged coaxially such that at least one of the inputs and one of outputs, respectively, can be optically connected to each other at a time. According to a further embodiment, a plurality of such input/output pairs can be formed at a time for providing two or more optical pathways.

The light source and light relay arrangement described above has the advantage that several different kinds of light sources can be conveniently incorporated into a single device without considerably increasing the amount of other optics in the device. Thus, the light relay acts as "an optical control centre" of the apparatus, guiding light to the measurement optics in a centralized manner. The measurement flexibility increases, as the optical relay may serve so as to guide light from the light sources to several measurement subunits, such as fluorescence measurement optics, absorption measurement optics, and/or to either the upper or lower side of the microplate.

The number of second light sources is typically 1-10, in particular 2-4.

By stating that two subunits of the apparatus are "optically connected or connectable", we mean that there is provided a direct optical link between the subunits, for example, by optical fibers or through direct visual connection, or that the device comprises means for easily connecting and disconnecting said link by suitable optical means, such as pivotable or movable mirrors, optical fiber connections, prisms or the like.

BRIEF DESCRIPTION OF DRAWINGS

The embodiments of the invention will be described more closely with reference to the attached drawings, in which.

DETAILED DESCRIPTION OF THE EMBODIMENTS

Figure 1:
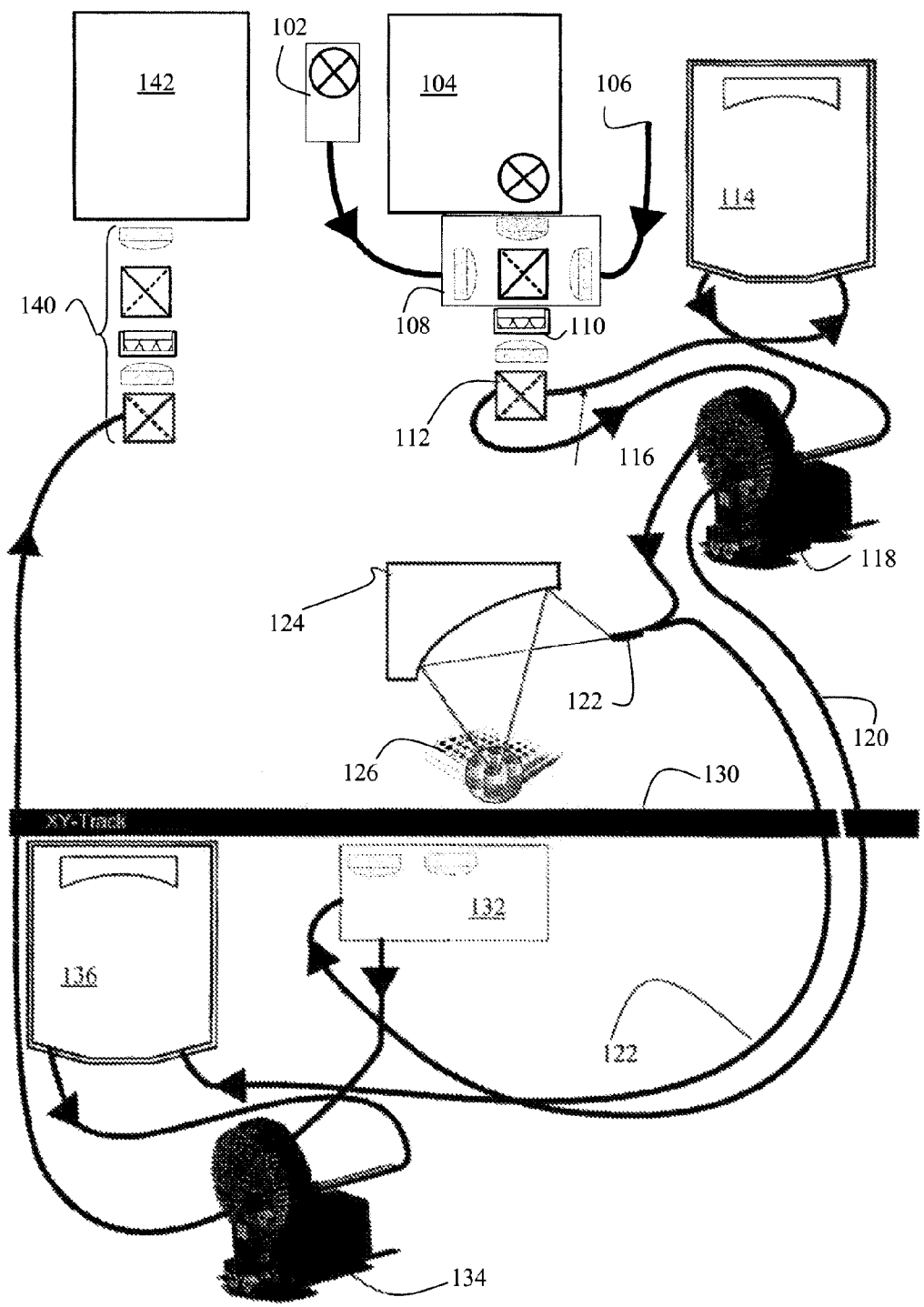
FIG. 1 represents an exemplary measurement set-up as a system-level scheme, including necessary equipment for both fluorescence and absorption measurements.

Referring to FIG. 1, the multiple narrow-band light source module used in fluorescence measurements is denoted with the reference numeral 102. The module is connected by an optical fiber or fiber bundle to a first light source selector module 108. To the first selector module 108 is also connected a wide-band light source 104. In this example, the selector module comprises also a third input 106 for a third light source type. The light is directed to a movable mirror 112, which is used for choosing the mode of operation. In absorbance measurements, wide-band light is conveyed to a sample site of a microtiter plate 126. In fluorescence measurement, narrow-band light is conveyed to a monochromator 114, from which the light is further guided to the sample site of the microtiter plate 126.

For selecting whether the absorption/excitation light is directed to the sample site from above or from below, a light relay 118 is provided in the optical path between the mirror 112 and the microtiter plate 126.

Accordingly, the apparatus is provided with means for collecting the transmission/emission light from the sample sites. Such means may comprise a concave light-focusing mirror 124, as in the present example on top of the sample sites, or a lens element 132, as in the present example below the sample sites. In fluorescence measurements, the emission light is directed to a second monochromator for preventing wavelengths outside the region of interest to be blocked. In absorption measurements, the transmitted light is not conveyed to the monochromator. A second light switch 134 may be provided in order to optically connect the transmission/monochromatized emission light to a detector 142. Suitable optical means 140, such as mirrors, lenses and collimators may be provided before the detector.

The sample holder is schematically denoted with the reference numeral 130 in the Figure. The sample holder is adapted to move two-dimensionally (on XY-track) between the excitation/emission optics such that any of the plurality of sample sites contained in a microtiter plate placed on the holder can be subjected to measurement.

The narrow-band light sources within the first light source may be light-emitting diodes (LEDs), the emission bands of which are less than 100 nm, typically 30-70 nm (at 10% intensity level). According to one embodiment, the emission bands of the LEDs at least slightly overlap with each others emission bands. That is, the wavelength bands of at least two of the plurality of LEDs overlap, the light intensity at the overlap wavelength being at least 10% of the peak wavelength of the dimmer of the LEDs. If two or more LEDs are arranged this way, a continuous emission light spectrum on a range having a width of at least 100 nm, typically at least 200 nm, even more than 500 nm, can be produced by choosing a right LED for light production. Together with using a single tunable monochromator, this embodiment practically allows for selection of any narrow wavelength within that range to be used for excitation of the sample. The excitation light has been found to be of high quality. That is, practically no light is directed to the sample at its emission wavelength. The excitation and emission wavelengths of typical markers used in biomedical analyses differ from each other by 10-100 nm.

Both ultraviolet and visible light sources can be used within the present invention either separately or in combination. According to one embodiment, the LEDs substantially cover the wavelength range 260-1000 nm, in particular 365-940 nm, typically at least 450-600 nm. Thus, the most common excitation wavelengths of marking agents can be covered. According to one embodiment, there are provided LEDs having peak wavelength at one, several or all of the following: 365 nm, 375 nm, 450 nm, 460 nm, 500 nm, 525 nm, 590 nm, 630 nm, 640 nm Typically LEDs of the "Power LED"-type are used.

Figure 6:
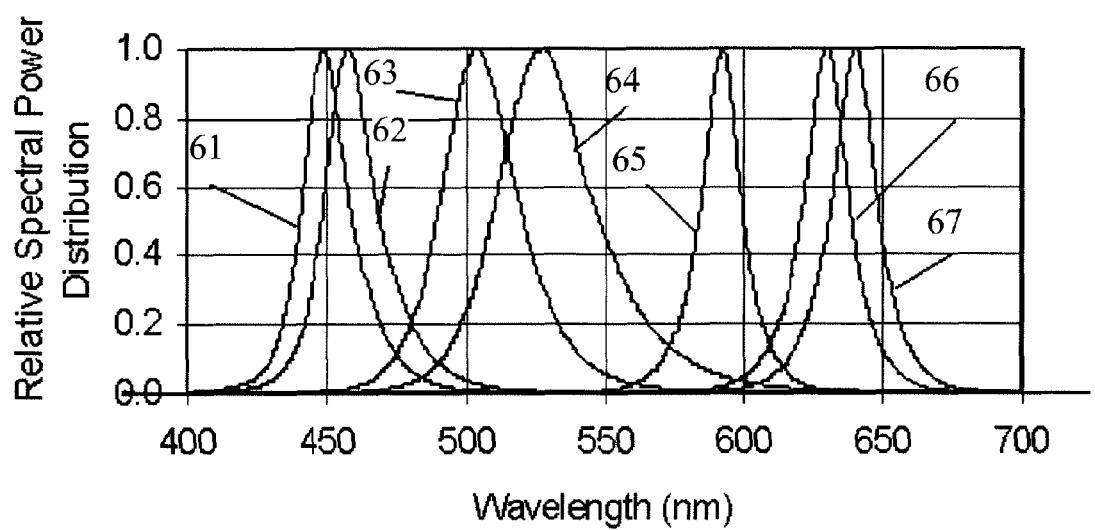
FIG. 6 illustrates exemplary spectra of commercially available LED light sources.

FIG. 6 illustrates the spectrum achievable using a light source comprising a series of PHILIPS LUXEON III Star power LEDs (for further details of the characteristics of the LEDs, see Technical Datasheet DS46/Luxeon/Philips. Another usable LED series for the present device are the Nichia Power LED series, which also cover UV wavelengths (e.g. the i-LED series).

Figure 2:
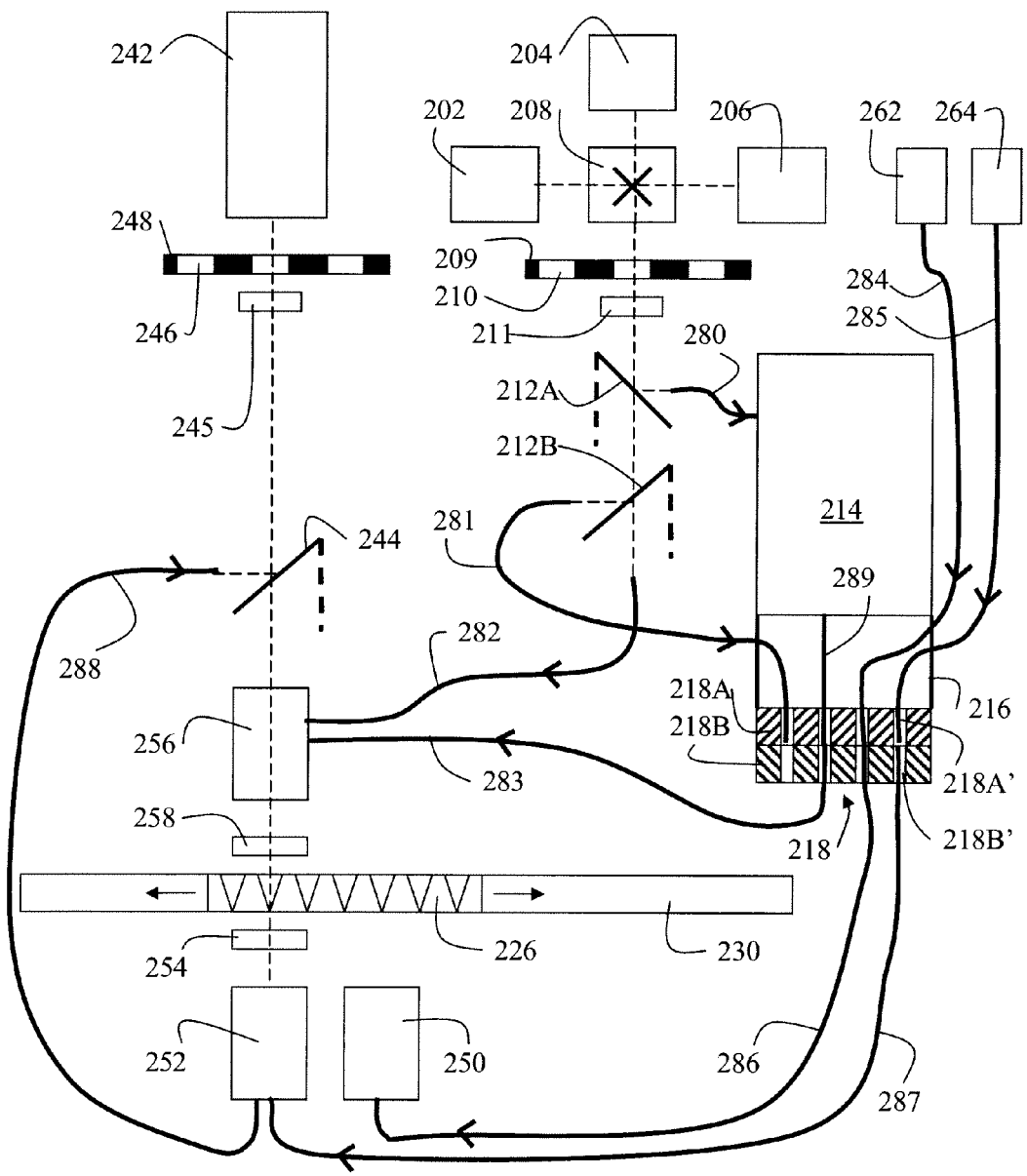
FIG. 2 illustrates another embodiment of the system.

FIG. 2 depicts another embodiment of the present system. The apparatus comprises, as the first light source 206, a narrow-band light source as described above. Light emitted by the first light source 206 is guidable to a monochromator 214 via optical fiber 280 for further reducing the wavelength band of the light. From the monochromator 214, monochromatized light is guided via optical fiber 289 to a first input of a light relay 218.

The input side of the light relay comprises an input member 218A, which contains a plurality of inputs 218A' and the output side of the light relay comprises an output member 218B, which contains a plurality of outputs 218B'. Further, the input member 218A and the output member 218B are movable with respect to each other such that at least one of the inputs 218A' in aligned with at least one of the outputs 218B' at a time for providing and optical connection between them. Also several such connections may be formed at a time.

The apparatus comprises means for guiding light from the light relay 218 successively to each of the sample sites of the sample plate 226 and for detecting light individually from said sample sites is turn. For this purpose, the sample plate 226 may be movable in two dimensions for allowing measurement of all sample sites of the sample plate 226. For this purpose, there may be provided a XY-track 230.

From the output side of the light relay 218, light is guided, depending on the measurement mode, either to upper or to lower side of the microtiter plate 226 for upper or lower sample excitation, respectively. In FIG. 2, the optical fiber 283 is used for upper excitation and the optical fiber 287 for lower excitation. Optical blocks 256, 252, respectively, are provided for directing the light excitation light towards the sample well to be measured. They also allow emission light to be passed to a detector 242. For this purpose, the blocks 256, 252 may contain a hinged or semitransparent mirror or the like optical arrangement. Lenses 258, 254 are typically provided between the blocks 256, 252 for giving the light beam hitting the sample a desired shape.

On emission side of the device, there are means for collecting the light emitted by the sample due to the excitation, and means for detecting the intensity of the collected light. The emission light collected from the sample by the upper of lower optical block 256, 252, depending on the measurement mode, is guided by to the detector 242. As the detector typically has only one input route, there may be provided a hinged or semitransparent mirror 244. In this example, emission light collected from below the plate 226, is guided via an optical fiber and reflected from the mirror 244, which is in first position, to detection optics Emission light collected from above the plate 226 is guided directly to the detection optics. The detection optics may comprise a lens 245 and a filter bank 248 containing a plurality of emissions filters 246.

As illustrated in FIG. 2, the apparatus may comprise also one or more second light sources 202, 204, 262 and 264. These may include one or more wide band or monochromatic light sources, or both. The wide band light sources are arranged such that their emission light is guided to the optical relay partially along the sample optical path than light from the first light source, that is, in a light source entity comprising only unmonochromatic light sources. For this purpose, there may be provided a light source selector 208 having a turnable mirror or mirrors. Light from the wide band light sources is typically used for absorption/transmission measurements, whereby it is guided to the samples unmonochromatized. For achieving this, there is provided a first hinged mirror 212A, which can be placed in a position that reflects light either to the monochromator (first light source used) or directly to the light relay (second light source used). Further, there may be provided a second hinged mirror 212B, whose purpose is to guide light to the light relay or directly to the upper of lower optical block 256, 252, thus by-passing both the monochromator and the light relay.

According to one embodiment, the apparatus comprises at least one second light source that is optically connected directly to a second input of the light relay. Such a light source may be a laser source, which can, in addition to the first light source, be used for fluorescence or ALPHASCREEN measurements.

According to one embodiment, the apparatus comprises at least one wide band second light source 202, 204, and at least one monochromatic second light source 262, 264. According to a further embodiment, the apparatus comprises both a continuous and a flashing second wide band source, such as a CERMAX unit and a Xenon flash. According to a further embodiment, the apparatus comprises both a continuous and a pulsed monochromatic second light source, such as a laser.

There may be provided, before the monochromator 214, optics, such as a lens 211 and a filter bank 209, which comprises one or more individual filters 210. The purpose of these filters is to allow selection of more exact wavelength band of the wide band second light sources, that may be present.

The present embodiments allow several kinds of measurements can be carried out, including fluorescence and time-resolved fluorescence, absorption, transmission, ALPHASCREEN using one apparatus only.

As the light initially has relatively narrow band (100 nm at maximum measured at 10% level), we have found that a single monochromator is sufficient for producing high-quality light whose wavelength can be selected not to overlap significantly with the emission wavelength of the sample. A single monochromator has the benefit of keeping the costs of the device at lower level. Of course, double or higher order monochromators can be used too. Such monochromators may be desirable, if also light from a wide-bandwidth lamp, such as a flash lamp (e.g. Xenon) or continuous lamp (e.g. CERMAX) or the like is to be monochromatized by the monochromator by a suitable light-guiding arrangement.

Output of the monochromator is connected to the first input the light relay. For this purpose, there may be provided an optically transparent quartz bar or the like rigid light guide. According to one embodiment, the monochromator and the optical relay are formed as a single unit, wherein there is a direct optical visibility between the output of the monochromator and the first input of the relay.

The light relay comprises a first input optically connected to the output of the monochromator, and at least one second input optically connected (by direct optical fiber 284 or 285) or connectable (by means of the hinged mirror 212A) to a second light source. As shown in FIG. 2, one or more of the outputs of the light relay are in optical connection to the sample sites for providing measurement light therein. According to one embodiment the light relay comprises two outputs being adapted for guiding light from selected input of the light relay to the sample sites optionally from above or from below of the sample plate 226.

According to one embodiment, light directed to the sample can be individually selected to originate from one of the light sources at a time. According to one embodiment, the inputs 218A' of the light relay are arranged in circumferential manner to an input member 218A and the outputs 218B' of the light relay are arranged in circumferential manner on an output member 218B facing the input member 218A and being rotatable with respect to the input member 218A for achieving selection of light to be guided to the sample sites. According to a further embodiment, the input and output members 218A, 218B are arranged coaxially such that at least one of the inputs and one of the outputs, respectively, can be optically connected to each other at a time. The input member 218A or the output member 218B, typically the output member 218B, may comprise a gearing, toothing or the like, which is connected to an electrically actuated motor, such as a stepper motor, for rotating the member into a desired position.

According to one embodiment, the optical relay allows the inputs 218A' of the light relay to be optically connected freely with any of the outputs 218B' of the relay one at a time, depending on the desired measurement mode. In some special measurement modes, also several outputs may be utilized at a time.

Light is guided to the inputs 218A' of the optical relay 218 and from the outputs 218B' of the optical relay 218 by means of optical fibres, whose ends can be aligned with each other in order to provide optical connection between a selected input and a selected output. According to one embodiment, the diameter of the input fibres is chosen to be smaller than the diameter of output fibres. Thus, all light emitted by the ends of the input fibres is collected by the output fibres. In particular, when a rotating light relay construction is used, this feature has been found to be of importance for securing lossless light transmission through the light relay 218, because of the achievable tolerances of the rotation mechanics and overall thinness of the fibres According to one embodiment, the monochromator 214 and the optical relay 218 are in firm mechanical contact with each other. That is, they are mounted in fixed position relative to each other. This allows a special kind of optical connection between the units, namely by a rigid optical fiber, such as a quartz rod. This is beneficial, as it makes the optical connection between the units very robust. Manufacturing these units as a single mechanical entity allows also control electronics of the monochromator and the light relay to be manufactured in a single control unit located in their vicinity.

Figure 3:
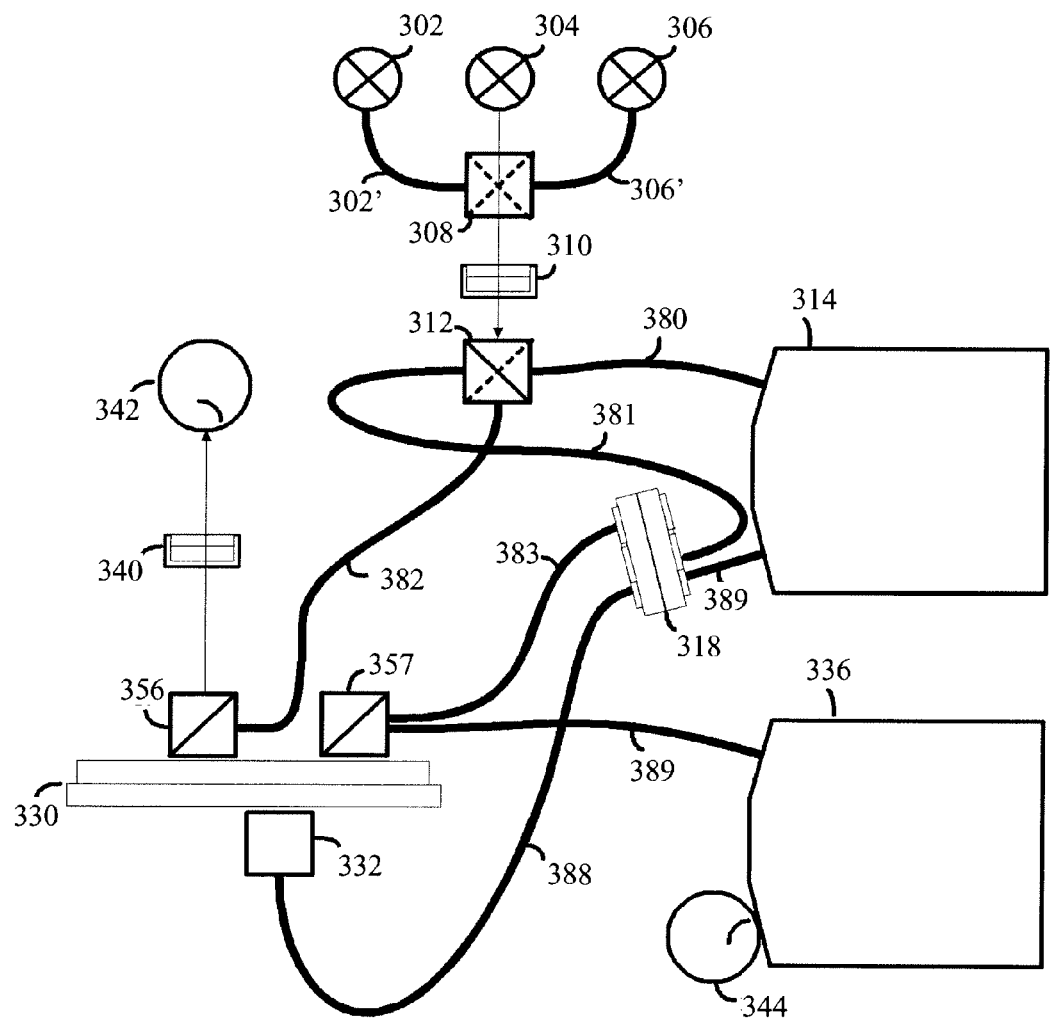
FIG. 3 illustrates still another embodiment of the system.

FIG. 3 illustrates still another embodiment of the system. The reference numerals 3xx mainly correspond to those of FIG. 1 (1xx). However, in this system, the light relay and one light detector on the emission side of the device is replaced with two individual light detectors 344 and 342, from which the first is connected to a monochromator and the other one is not. This allows for more versatile measurements, as detectors having different properties can be used.

As illustrated in FIG. 3, the apparatus may comprise an optics module 357 placed typically on top of the sample plate and comprising an input for excitation light (from fibre 383) and an output for emission light (to fibre 389). According to one embodiment, the optics module 357 comprises an excitation lens for focusing the excitation light to an individual sample space of the sample plate and an emission lens, separate from the excitation lens, for collecting emission light from the sample space. That is, the excitation and emission light are conveyed through separate optical channels in the optics module 357. However, there may be provided also one or more mirrors in the optics module that is/are common to both channels. In addition to focusing lenses, the channels may separately also contain mirrors and/or optical fibres.

As illustrated in FIG. 3, according to one embodiment, the output fibre of the optics module 357 is connected to an output monochromator 336 and further to the detector 344. The detector 344 downstream the monochromator 366 may also be employed for detecting emission light excited through a second optics module 332 placed below the sample plate and collected using the first optics module 357. On the other hand, the other detector 342 not typically coupled to a monochromator may be used to detect emission light excited through fibres 382 or 388 or in absorption measurements using, for example, the fibre 388 for transmitting broadband light to the sample through the second optics module 388 and collecting the transmitted light by a third optics module 356. It is clear from FIG. 3, that the optical relay 318 is the key element, in addition to the light source and light source selecting arrangement 302-314, in selecting the desired measurement mode out of the several possibilities herein described.

Figure 4:
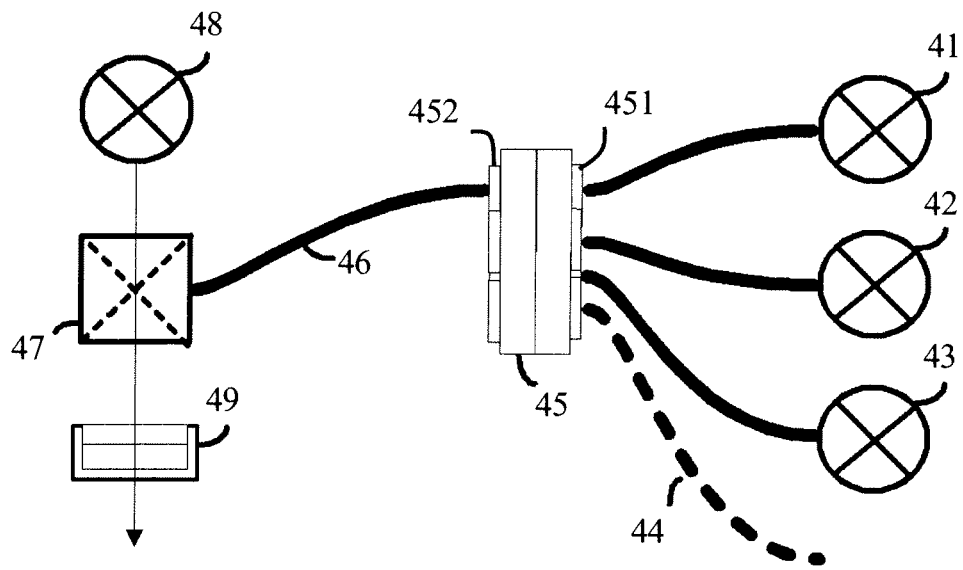
FIG. 4 depicts a multiple-narrow-band light source according to one embodiment of the invention.

With reference to FIG. 4, the first light source comprises means for selecting which one of the individual light sources is optically coupled to the sample sites. According to one embodiment, the individual light sources 41, 42, 43 (optionally also more) are optically connected by means of optical fibers to a narrow-band light source selector unit 45 that provides an optical pathway between one of the optical fibres and the output 452 of the first light source. There may be one or more further input channels 44 for additional individual light sources (in addition to the three explicitly illustrated in FIG. 4). The output 452 may also comprise a fiber optic connection 46 to further optics of the device (that is, typically another light source selector 47, corresponding to the light source selectors 108, 208, 308 introduced with reference to FIGS. 1, 2 and 3, respectively). The individual light sources 41, 42, 43 may be mounted on a separate light source module having an optical fiber connector for each of the individual light sources 41, 42, 43.

The narrow band light source selector may comprise a first rotating or translating element and a second static element, whereby the selection of the light source is determined by the relative positions of the first and second elements. For example, the ends of the optical fibres can be mounted circumferentially on an input wheel, which is rotatable such that one of the fibers at a time is aligned with an output fibre. Alternatively, the output fibre may be movable. Such an arrangement is illustrated in FIG. 4, wherein the inputs 451 and output 452 are mounted on elements, whish may be rotatable or translatable with respect to each other such that the mutual optical connection between the light sources 41, 42, 43 and the output 452 changes.

The plurality of light sources can also be directly mounted on a movable (typically translatable or rotatable) frame, whereby each one of the light sources can be individually optically coupled with the sample sites by movement the movable frame, for example, by aligning the light source with an output fibre, one end of which is arranged in the vicinity of the frame.

It has become apparent from the above that the apparatus may include a cascade of light source selectors: one in the first light source for choosing the individual narrow band light source; one downstream the first light source for selecting whether the first light source or some other light source is used; and one (the light relay) for finally choosing the desired measurement mode. It has shown that this kind of arrangement provides cost-effective manufacture, and versatile and flexible use of the device, allowing not only fluorescence measurement, but also other types of common measurements.

Figure 5:
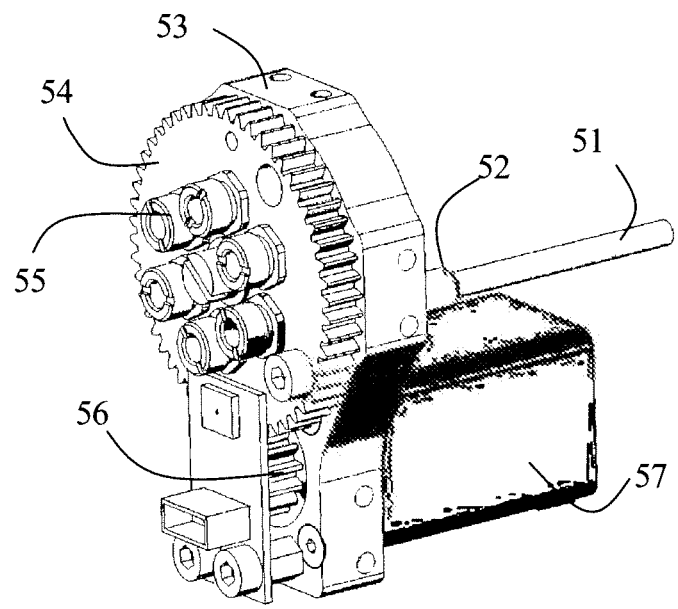
FIG. 5 illustrates in a perspective view in detail the light relay according to one embodiment of the invention.

FIG. 5 shows an exemplary embodiment of the optical relay which can be used for changing the mode of operation of the device (i.e., a relay corresponding to parts 118, 218 and 318 of FIGS. 1, 2 and 3, respectively). The relay comprises body 53, which comprises a plurality of inputs. Show in the figure is input 52, to which a quartz rod 51 from the excitation monochromator is connected. On the output side there is a toothed output wheel 54, which is rotatable. The rotation is achieved by rotating a toothed gear wheel 56, which co-operates with the output wheel 54. The gear wheel 56 is rotatably connected to a stepper motor 57. A plurality of outputs 55 are arranged on the output wheel 54. The outputs 55 are suitable for engagement with optical fibers or optical fiber connectors.

According to one embodiment, the detector of the apparatus is a photomultiplier tube (PMT). Other kinds of detectors may be employed too.

Also several detectors may be arranged in parallel and means for optically switching between the detectors may be provided. This allows for the most suitable detector for the wavelength/intensity to be used.

Also several detectors may be arranged in parallel and means for optically switching between the detectors may be provided. This allows for the most suitable detector for the wavelength/intensity to be used.

The embodiments described above and presented in the attached drawings are provided for illustrative purposes and do not limit the scope of the invention defined in the appended claims. The embodiments may be combined in order to achieve even more versatile systems. In particular, the light source arrangements, in particular, teachings concerning the structure and operation of the multiple-narrow-band light source, as well as the structure and operation of the light relay for selecting the operation mode of the device can be freely applied to each of the exemplified embodiments and also those variations not herein discussed in detail.

The invention claimed is:

1. An apparatus for optically analyzing samples contained in sample sites of a sample holder by means of fluorescence, comprising
    a light source comprising a plurality of individual light sources having narrow wavelength bands,
    a light source selector for selecting light from one of the individual light sources by selecting and connecting an optical fiber with light from one of said individual light sources,
    a wavelength-tunable single monochromator for further reducing the wavelength band of the light emitted by said selected individual light source,
    means for guiding the reduced selected individual light source light to the sample sites of the sample holder, and
    a detector for detecting light from the sample sites.

2. The apparatus according to claim 1, wherein the individual light sources are LEDs (light emitting diodes).

3. The apparatus according to claim 1, wherein the wavelength bands of at least two of the plurality of individual light sources overlap.

4. The apparatus according to claim 1, wherein the individual light sources are mounted on a light source module, from which the individual light sources are optically connected by means of optical fibers to the light source selector.

5. The apparatus according to claim 1, wherein the light source selector comprises a first rotating or translating element and a second static element, whereby the selection of the individual light source is determined by the relative positions of the first and second elements.

6. The apparatus according to claim 1, wherein the plurality of light sources are mounted on a movable frame, whereby each one of the light sources can be individually optically coupled with the sample sites by movement by the movable frame.

7. The apparatus according to claim 1, wherein the monochromator is a grating-based tunable monochromator.

8. The apparatus according to claim 1, comprising means for automatically selecting the individual light source used based on given properties of a marking agent used in the sample, wherein the wavelength band of the light source is within the absorption wavelength of the marker but does not significantly overlap with the emission wavelength of the marking agent.

9. The apparatus according to claim 1, comprising;
a light relay having at least one optical input being connected to said monochromator, and
said light relay has two outputs adapted to guide light from the input to one of at least two light detectors for detecting from the sample sites.

10. The apparatus according to claim 1, comprising a second monochromator for selecting a wavelength of interest to the detector.

11. The apparatus according to claim 1, comprising a filter or a plurality of filters, the number of filters being smaller than the number of individual light sources in the first light source, for preventing higher-order wavelengths passing the monochromator from entering the sample sites, said filter(s) optionally being the only filter(s) on the excitation side of the apparatus.

12. The apparatus according to claim 11, comprising means for automatically selecting one of the plurality of filters depending on other measurement parameters.

13. The apparatus according to claim 1, wherein the detector is a photomultiplier tube (PMT).

14. The apparatus according to claim 1, comprising a
frame for accommodating the sample holder such that it is optically accessible from above and from below,
means for directing excitation light to the sample sites of the sample holder from above or below, and
means for collecting emission light from the sample sites from above.

* * * * *